(12) United States Patent
Aisaki

(10) Patent No.: US 6,405,089 B1
(45) Date of Patent: Jun. 11, 2002

(54) DC-AC ELECTRIC POTENTIAL TREATMENT APPARATUS

(76) Inventor: Shiga Aisaki, 545-6, Naka-Kiyoto 1-chome, Kiyose-shi, Tokyo 204-0012 (JP)

( * ) Notice: Subject to any disclaimer, the term of this patent is extended or adjusted under 35 U.S.C. 154(b) by 0 days.

(21) Appl. No.: 09/598,471

(22) Filed: Jun. 22, 2000

(30) Foreign Application Priority Data

Oct. 22, 1998 (JP) .......................................... 10-300673

(51) Int. Cl.7 ................................................ A61N 1/18
(52) U.S. Cl. ............................................ 607/66; 607/3
(58) Field of Search ..................... 607/1–3, 66, 115

(56) References Cited

U.S. PATENT DOCUMENTS 6,021,348 A * 2/2000 James ............................ 607/3
6,029,090 A * 2/2000 Herbst .......................... 607/66
6,173,204 B1 * 1/2001 Sullivan et al. ................. 607/5

FOREIGN PATENT DOCUMENTS

JP 4-28597 * 5/1991

* cited by examiner

Primary Examiner—George R Evanisko
(74) Attorney, Agent, or Firm—Liniak, Bernato, Longacre & White

(57) ABSTRACT

A DC-AC electric potential treatment apparatus of the present invention can freely switch high potential AC and high potential DC. The DC-AC electric potential treatment apparatus comprises an electric cloth having a treatment lead for outputting high potential AC or high potential DC, a DC-AC power supply circuit for supplying high potential DC and high potential AC to the treatment lead, and a DC-AC switch circuit for switching the supply from the DC-AC power supply circuit to the treatment lead between high potential DC and high potential AC.

1 Claim, 1 Drawing Sheet

DC-AC ELECTRIC POTENTIAL TREATMENT APPARATUS

BACKGROUND OF THE INVENTION

1. Field of the Invention

The present invention relates to an electric potential treatment apparatus which has an electric cloth with a treatment lead outputting high electric potential and which a patient sit down on the electric cloth for treatment, and more particularly relates to a DC-AC electric potential treatment apparatus which can switch high potential DC and AC and apply it to the treatment lead.

2. Description of Related Art

An electric potential treatment apparatus comprises an electric cloth having a treatment lead which outputs high potential of an effective value of 9 kV or below. The curative effects of the electric potential treatment apparatus to a patient seated on the electric cloth are the improvement of his blood circulation, the improvement of his constitution and the improvement of other conditions. The treatment lead is made of a plate of substantially carbon or a fiber woven plate of carbon fiber and has positive and negative lead wires fixed. Further, the electric cloth is formed like a cushion that the treatment lead is covered with an insulator, e.g., vinyl on a cotton cloth and that it is spread with a covering. In the electric potential treatment apparatus, the high potential current is applied to the treatment lead to output the high potential therefrom.

The electric cloth of the electric potential treatment apparatus is covered with the cold insulator, which gives the unpleasant feelings to the patient. In order to solve the problem, a heating electric potential treatment apparatus having an electric cloth with a heater for keeping warmth is disclosed in the Japanese Patent Publication No. 62-20220 and the Japanese Patent Publication No. 4-28597. The operation of the heating electric potential treatment apparatus disclosed in the Japanese patent No. 4-28597 is that the electric cloth is heated with the heater for keeping warmth and that high potential AC (9 kV) is automatically applied to the treatment lead when the temperature of the electric cloth reaches a predetermined temperature. Further, after a predetermined time elapses, the high potential applied to the treatment lead is automatically decreased to a predetermined potential, e.g., 3 kV and this potential is applied to the treatment lead. With the described operation, the heating electric potential treatment apparatus automatically switches the heating of the electric cloth, the high potential AC output (9 kV) from the treatment lead, and the predetermined potential AC output (3 kV) from the treatment lead.

In the conventional electric potential treatment apparatus, other than the electric potential treatment apparatus which outputs high potential AC to the treatment lead such as the above-described heating electric potential treatment apparatus, there is an electric potential treatment apparatus witch outputs high potential DC. It should be noted that the effects of the DC and AC treatment are the same such as the improvement of the blood circulation or the improvement of the constitution. In a case of AC treatment, the vibration is given to a human body but in a case of DC treatment, no vibration is given to the human body. Further, depending on the patient, he may receive a great curative effect from either one of DC and AC treatment.

When plural people use the electric potential treatment apparatus at home, the curative effect of AC and DC treatment is varied depending on the person. Even one person uses the electric potential treatment apparatus, he may want to receive the both DC and AC treatments. However, the conventional electric potential treatment apparatus output either DC or AC not both. Therefore, in order to perform both AC and DC treatments, two treatment apparatus:

DC electric potential treatment apparatus and AC electric potential treatment apparatus are required.

In Japanese law, for a treatment apparatus having two or more functions, it must be the structure that two or more functions cannot be used at the same time.

BRIEF SUMMARY OF THE INVENTION

It is an object of the present invention to provide a DC-AC electric potential treatment apparatus which can switch and output high potential DC and high potential AC.

A DC-AC electric potential treatment apparatus according to the present invention an electric cloth having a treatment lead for outputting high potential AC or high potential DC, a DC-AC power supply circuit for supplying high potential DC and high potential AC to the treatment lead, and a DC-AC switch circuit for switching the supply from the DC-AC power supply circuit to the treatment lead between high potential DC and high potential AC.

According to the DC-AC electric potential treatment apparatus of the present invention, high potential DC and AC are switched to supplied to the treatment lead. Therefore, only one DC-AC electric potential treatment apparatus can perform both DC treatment and AC treatment.

PREFERRED EMBODIMENTS OF THE INVENTION

Figure 1:
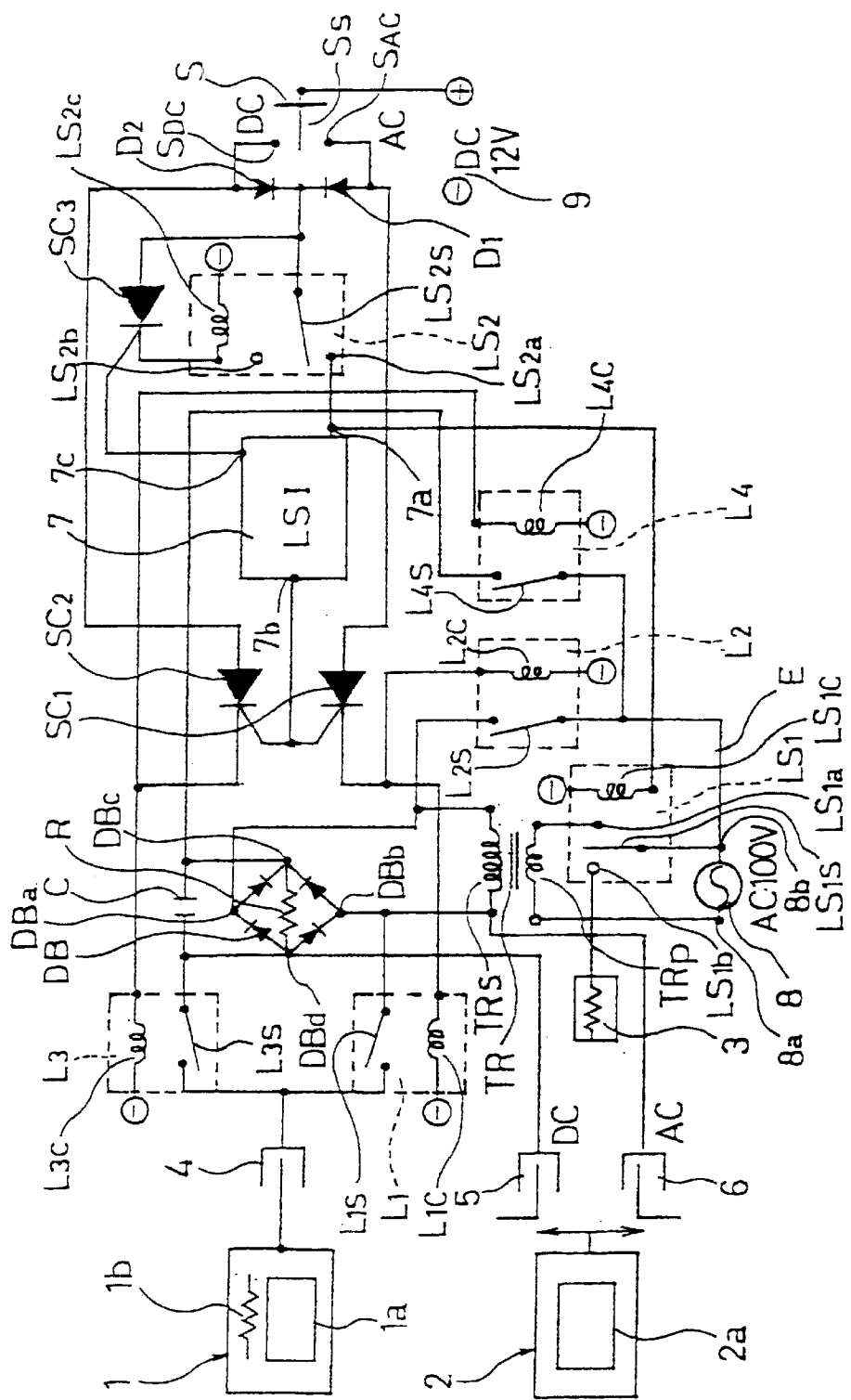
FIG. 1 is a circuit diagram of a DC-AC electric potential treatment apparatus according to one embodiment of the present invention.

The preferred embodiments of the present invention will be described hereinafter with reference to the accompanying drawing. In the following description and the drawing, the same reference numerals are used for the same components and repetitive description on the same components will be omitted.

FIG. 1 shows a circuit diagram of a DC-AC electric potential treatment apparatus according to one embodiment of the present invention.

First, the constitution of the circuit of the DC-AC electric potential treatment apparatus will be described. The circuit shown in FIG. 1 comprises a DC-AC power supply circuit, a DC-AC switch circuit, a double-pole switch S and electric cloths 1, 2 each having a treatment lead 1a, 2a and a heater for keeping warmth 1b, 3, respectively. It should be noted that there is a power supply circuit (not shown) for a heater for supplying power to the heaters 1b, 3 in the circuit of FIG. 1.

The constitution of the DC-AC power supply circuit will be described.

The DC-AC power supply circuit comprises an AC power supply (100 V AC) 8, a high potential transformer TR, a diode bridge circuit DB, a high voltage resistor R and a capacitor C. The DC-AC power supply circuit inputs 100 V AC and outputs 12 kV DC and 9 kV AC.

The AC power supply 8 outputs 100 V AC. One end 8a of the AC power supply 8 is connected to one end of a primary $TR_P$ of the transformer TR and the other end 8b thereof is connected to the other end of the primary $TR_P$ of the transformer TR through a relay switch $LS_1$. The AC power supply 8 connected by the above-described manner supplies 100 V AC to the transformer TR when a moving contact $LS_{1S}$ of the relay switch $LS_1$ is closed to a fixed contact $LS_{1a}$.

The high potential transformer TR generates the high potential of 9 kV AC at a secondary $TR_s$ when 100 V AC is supplied to the primary $TR_P$. The secondary $TR_S$ of the transformer TR is connected to terminals $DB_a$, $DB_b$ of the diode bridge circuit DB. Further, the secondary $TR_S$ of the transformer TR is connected to one end of an open contact $L_{1S}$ of a high voltage reed relay $L_1$ and one end of an open contact $L_{2s}$ of a high voltage reed relay $L_2$. Further, when the open contact $L_{1S}$ of a high voltage reed relay $L_1$ and the open contact $L_{2s}$ of the high voltage reed relay $L_2$ are closed, 9 kV AC is supplied to an outlet 4.

Further, the secondary $TR_s$ of the transformer TR is connected an outlet 6 and 9 kV AC is also supplied to the outlet 6.

The diode bridge circuit DB is a full-wave rectifier circuit using four diodes. The capacitor C and the high voltage resistor R are connected between nodes $DB_c$ and $DB_d$ of the diode bridge circuit DB. The capacitor C is a smoothing element for removing ripple. The high voltage resistor R is an element for discharging the charges charged in the capacitor C to decrease the arc discharge. When 9 kV AC is supplied to the diode bridge circuit DB from the transformer TR, 12 kV DC is charged between the nodes $DB_c$ and $DB_d$ (in the capacitor C). It should be noted that the four diodes used in the diode bridge circuit DB have high voltage resistance.

The ends of the capacitor C are connected to one end of an open contact $L_{3s}$ of a high voltage reed relay $L_3$ and one end of an open contact $L_{4s}$ of a high voltage lead relay $L_4$, respectively. When the open contact $L_{3s}$ of the high voltage reed relay $L_3$ and the open contact $L_{4s}$ of the high voltage lead relay $L_4$ are closed, 12 kV DC is supplied to the outlet 4. The voltage resistance of the capacitor C is preferably about 15 kV. The capacitor C is connected to the outlet 5 at the end and 12 kV DC is applied to the outlet 5.

The high voltage resistor R has the resistance of 100 M Ω, which rapidly discharges the charges of the capacitor C. With the high voltage resistor R, 12 kV DC of the capacitor C is decreased to 3 kV in five second discharge. The reason why the high voltage resistor R is used for the voltage drop is to decrease the arc discharge since the arc drags if sparks occur between the nodes due to DC. The voltage resistance of the high voltage resistor is preferably 15 kV.

Next, the configuration of the DC-AC switch circuit will be described.

The DC-AC switch circuit comprises two relay switches $LS_1$, $LS_2$, LSI 7, three thyristors $SC_1$, $SC_2$, $SC_3$ and four high voltage reed relays $L_1$, $L_2$, $L_3$, $L_4$. The DC-AC switch circuit switches and outputs 12 kV DC and 9 kV AC supplied from the DC-AC power supply circuit to the outlet 4. It should be noted the switch is commanded through the double-pole switch S.

The relay switch $LS_1$ is to switch whether 100 V AC from the AC power supply 8 is supplied to the high potential transformer TR. One end of a coil $LS_{1c}$ of the relay switch $LS_1$ is connected to a fixed contact $LS_2$a of the relay switch $LS_2$. The moving contact $LS_{1s}$ is connected to one end of the AC power supply 8. The fixed contact $LS_{1a}$ is connected to one end of the primary $TR_P$ of the high potential transformer TR. It should be noted that the fixed contact $LS_{1b}$ is open.

In the relay switch $LS_1$, when the current is supplied to the coil $LS_{1c}$, the moving contact $LS_{1s}$ is closed to the fixed contact $LS_{1b}$.

The relay switch $LS_2$ outputs 12 V DC to the LSI 7 and the relay switch $LS_{1s}$, drives a timer of LSI 7 and switches the movable contact $LS_{1s}$ of the relay switch $LS_1$. One end of the coil $LS_{2c}$ of the relay switch $LS_2$ is connected to a cathode of the thyristor $SC_3$. Further, the movable contact $LS_{2s}$ is connected to an anode of the thyristor $SC_3$ and cathodes of the diodes $D_1$, $D_2$. Furthermore, the fixed contact $LS_{2a}$ is connected to a terminal $7_a$ of the LSI 7 and one end of the coil $LS_{1c}$ of the relay switch $LS_1$. It should be noted that the fixed contact $LS_{2b}$ is open. In the relay switch $LS_2$, when the current is supplied to the coil $LS_{2c}$, the movable contact $LS_{2s}$ is closed to the fixed contact $LS_{2b}$.

LSI 7 operates as a timer. The terminal $7_a$ of the LSI 7 is connected to the fixed contact $LS_{2a}$ of the relay switch $LS_2$. Further, a terminal $7_b$ of the LSI 7 is connected to gates of the thyristors $SC_1$, $SC_2$. Furthermore, a terminal $7_c$ of the LSI 7 is connected to a gate of the thyristor $SC_3$. When 12 V DC is applied to the terminal $7_a$, after five seconds the LSI 7 outputs the trigger current to the gates of thyristors $SC_1$, $SC_2$, and after one second, it outputs the trigger current to the gate of the thyristor $SC_3$.

The thyristor $SC_1$ and the high voltage reed relays $L_1$, $L_2$ operate when switched to AC. When the trigger current is supplied to the gate of the thyristor $SC_1$, the thyristor $SC_1$ is turned on and outputs the current to the coils $L_{1c}$, $L_{2c}$ of the high voltage reed relays $L_1$, $L_2$ from the cathode thereof. Then, the open contacts $L_{1s}$, $L_{2s}$ of the high voltage reed relays $L_1$, $L_2$ are closed, and 9 kV AC is supplied to the outlet 4.

The thyristor $SC_1$ operates when switched to AC to output the current to close the open contacts $L_{1s}$, $L_{2s}$ of the high voltage reed relays $L_1$, $L_2$. The anode of the thyristor $SC_1$ is connected to a fixed contact $S_{AC}$ of the double-pole switch S. The cathode of the thyristor $SC_1$ is connected to one end of the coils $L_{1c}$, $L_{2c}$ of the high voltage reed relays $L_1$, $L_2$. Further, the gate of the thyristor $SC_1$ is connected to the terminal $7_b$ of the LSI 7.

The high voltage reed relays $L_1$, $L_2$ is to switch whether 9 kV AC from the high potential transformer TR is supplied to the outlet 4. One end of the coils $L_{1c}$, $L_{2c}$ of the high voltage reed relays $L_1$, $L_2$ is connected to the cathode of the thyristor $SC_1$. Further, one end of the open contacts $L_{1s}$, $L_{2s}$ of the high voltage reed relays $L_1$, $L_2$ is connected to the secondary $TR_s$ of the high potential transformer TR. Furthermore, the other end of the open contact $L_{1s}$ of the high voltage reed relay $L_1$ is connected to the outlet 4. The other end of the open contact $L_{2s}$ of the high voltage reed relay $L_2$ is connected to a terminal 8b (ground E) of the AC power supply 8.

It should be noted that the voltage resistance of the high voltage reed relays $L_1$, $L_2$ are 15 kV. Because of this property, the reed relays $L_1$, $L_2$ are not damaged by the sparks (arc) due to a few kV AC when the open contacts $L_{3s}$, $L_{4s}$ are closed. Accordingly, other elements are not damaged by the damage of the reed relays $L_1$, $L_2$ or arc.

The thyristor $SC_2$ and the high voltage reed relays $L_3$, $L_4$ operate when switched to DC. When the trigger current is supplied to the gate of the thyristor $SC_2$, the thyristor $SC_2$ is turned on and outputs current to the coils $L_{3c}$, $L_{4c}$ of the high voltage reed relays $L_{3s}$, $L_{4s}$ from the cathode thereof. Then, the open contacts $L_{3s}$, $L_{4s}$ of the high voltage reed relays $L_3$, $L_4$ are closed to output 12 kV DC to the outlet 4.

The thyristor $SC_2$ operates when switched to DC to output the current to close the open contacts $L_{3s}$, $L_{4s}$ of the high voltage reed relays $L_3$, $L_4$. The anode of the thyristor $SC_2$ is connected to a fixed contact $S_{DC}$ of the double-pole switch S. Further, the cathode of the thyristor $SC_2$ is connected to one end of the coils $L_{3c}$, $L_{4c}$ of the high voltage reed relays $L_3$, $L_4$. Furthermore, the gate of the thyristor $SC_2$ is connected to the terminal $7_b$ of the LSI 7.

The high voltage reed relays $L_3$, $L_4$ is to switch whether 12 kV DC charged in the capacitor C is applied to the outlet 4. The cathode of the thyristor $SC_2$ is connected to one ends of the coils $L_{3c}$, $L_{4c}$ of the high voltage reed relays $L_3$, $L_4$. One end of the open contacts $L_{3s}$, $L_{4s}$ is connected to the respective end of the capacitor C. Further, the other end of the open contact $L_{3s}$ of the high voltage reed relays $L_3$ is connected to the outlet 4. The other end of the open contact $L_{4s}$ of the high voltage reed relays $L_4$ is connected to the terminal 8b (ground E) of the AC power supply 8.

It should be noted that the voltage resistance of the high voltage reed relays $L_3$, $L_4$ is 15 kV. Because of this property, the reed relays $L_3$, $L_4$ are not damaged by the sparks (arc) due to a few kV DC when the open contacts $L_{3s}$, $L_{4s}$ are closed. Accordingly, other elements are not damaged by the damage of the reed relays $L_3$, $L_4$ or arc.

Next, the configuration of the double-pole switch S will be explained.

The double-pole switch S is a switch to switch whether the supply to the treatment lead 1a is AC or DC, which is operated from the outside. The fixed contact $S_{AC}$ of the double-pole switch S is connected to the anode of the thyristor $SC_1$ and to the anode of the diode $D_1$. Further, the closed contact SDC of the double-pole switch S is connected to the anode of the thyristor $SC_2$ and to the anode of the diode $D_2$. Furthermore, the movable contact $S_s$ of the double-pole switch S is connected to the positive terminal of the DC power supply 9 (12 V DC). When the movable contact $S_s$ is closed to the fixed contact $S_{AC}$, 12 V DC is applied to the anodes of the thyristors $SC_1$, $SC_3$ and the relay switch $LS_2$. On the other hand, the moving contact $S_s$ is closed to the closed contact $S_{DC}$, 12 V DC is applied to the anodes of the thyristors $SC_2$, $SC_3$ and the relay switch $LS_2$. The double-pole switch S is operated by an operator.

Next, the constitution of the electric cloths 1, 2 will be described.

The electric cloths 1, 2 comprise the treatment leads 1a, 2a, respectively, and further comprise the heaters 1b, 3 for keeping warms. The DC-AC electric potential treatment apparatus of the present embodiment is used in the way that, for example, a person is seated on the electric cloths 1, 2 and that high potential DC or AC is applied from the treatment leads 1a, 2a. Further, the electric cloths 1, 2 are heated to keep warms by the heater 1b, 3.

It should be noted that the material and the construction of the electric cloths 1, 2 and the treatment leads 1a, 2a are not limited. For example, the material and the construction used in the conventional electric cloths and the treatment leads can be used. Further, the construction of the heaters 1b, 3 are not limited if they heat the electric cloths 1, 2 to the temperature suitable for the human body.

The electric cloth 1 is connected to the outlet 4. Then, 12 kV DC or 9 kV AC is supplied to the treatment lead 1a from the outlet 4. 30 V AC is supplied to the heater 1b of the electric cloth 1 from the transformer (not shown in FIG. 1) connected to the AC power supply 8. This transformer may be a power supply circuit for the heater disclosed in the Japanese Patent Publication No. 4-28597. It should be noted that when the high potential is not supplied to the treatment lead 1a, 30 V AC is supplied to the heater 1b from the outlet 4.

The electric cloth 2 is plugged to the outlet 5 or the outlet 6. 12 kV DC or 9 kV AC is supplied to the treatment lead 2a from the outlet 5 or 6, respectively. 30 V AC is supplied to the heater 3 from the transformer (not shown in FIG. 1) connected to the AC power supply 8. This transformer may be a power supply circuit for the heater disclosed in the Japanese Patent Publication No. 4-28597. It should be noted that when the high potential is not supplied to the treatment lead 2a, 30 VAC is supplied to the heater 3.

Next, the operation of the circuit of the AC-DC electric potential treatment apparatus will be described.

The present circuit starts operating when 100 V AC is applied from the AC power supply 8. It should be noted that a switch may be placed between the AC power supply 8 and the high potential transformer TR to start the operation of the circuit.

First, in a case of the output of 9 kV AC from the treatment lead 1a of the electric cloth 1 will be explained.

A user to use the AC-DC electric potential treatment apparatus operates to close the movable contact $S_s$ of the double-pole switch S to the fixed contact $S_{AC}$. Then, 12 V DC is applied to the movable contact $LS_{2s}$ of the relay switch $LS_2$ and the anode of the thyristor $SC_3$ through the diode $D_1$, and 12 V DC is applied to the anode of the thyristor $SC_1$.

When 12 V DC is applied, since the movable contact $LS_{2s}$ of the relay switch $LS_2$ is closed to the fixed contact $LS_{2a}$, 12 V DC is supplied to the LSI 7 and the coil $LS_{1c}$ of the relay switch $LS_1$ through the relay switch $LS_2$. Then, the timer of the LSI 7 is driven. Further, since the current flows to the coil $LS_{1c}$ of the relay switch $LS_1$, and the movable contact $LS_{1s}$ is closed to the closed contact $LS_{1b}$, the supply of 100 V AC from the AC power supply 8 to the primary $TR_P$ of the high potential transformer TR is stopped.

In the LSI 7, after five seconds the timer is driven, the trigger current is supplied to the gate of the thyristor $SC_1$ from the terminal $7_b$. It should be noted that in these five seconds, charges of 12 kV DC charged in the capacitor C are discharged by flowing into the high voltage resistance R and that voltage is dropped to 3 kV. In result, the generation of the arc at the switching of the high voltage reed relays $L_1$, $L_2$ is decreased.

After five seconds elapsed and further after one second, the trigger current is supplied to the gate of the thyristor $SC_3$ from the terminal 7 c of the LSI 7. In this one second, the open contacts $L_{1s}$, $L_{2s}$ of the high voltage reed relays $L_1$, $L_2$ are closed before 100 V AC is supplied to the primary $TR_P$ of the high potential transformer TR.

When the trigger current is supplied to the gate of the thyristor $SC_1$ from the terminal 7b of the LSI 7, the thyristor $SC_1$ is turned on, and the current flows to the coils $L_{1c}$, $L_{2c}$ of the high voltage reed relays $L_1$, $L_2$ from the cathode of the thyristor $SC_1$. Then, the open contacts $L_{1s}$, $L_{2s}$ of the high voltage reed relays $L_1$, $L_2$ are closed.

Further, when the trigger current is supplied to the gate of the thyristor $SC_3$ from the terminal 7 c of the LSI 7, the thyristor SC3 is turned on, and the current flows to the coil $LS_{2c}$ of the relay switch $LS_2$ from the cathode of the thyristor $SC_3$. Then, the moving contact $LS_{2s}$ of the relay switch $LS_2$ is closed to the fixed contact $LS_{2b}$, and the current supply from the relay switch $LS_2$ to the coil $LS_{1c}$ of the relay switch $LS_{1s}$ is stopped. Accordingly, the movable contact $LS_{1s}$ of the relay switch $LS_1$ is closed to the fixed contact $LS_{1a}$, and 100 V AC is supplied to the primary $TR_P$ of the high potential transformer TR from the AC power supply 8. Then, 9 KV AC is generated at the secondary $TR_s$ of the high potential transformer TR.

In result, the secondary $TR_s$ of the high potential transformer TR which generates 9 kV AC is connected to the outlet 4 through the high voltage reed relay $L_1$ at one end and to the ground E through the high voltage reed relay $L_2$ at the other end. Accordingly, the treatment lead 1a outputs 9 kV AC.

Next, in a case of the output of 12 kV DC from the treatment lead 1a of the electric cloth 1 will be explained.

A user to use the AC-DC electric potential treatment apparatus operates to close the movable contact $S_s$ of the switch S to the fixed contact $S_{DC}$. Then, 12 V DC is applied to the movable contact $LS_{2s}$ of the relay switch $LS_2$ and the anode of the thyristor $SC_3$ through the diode $D_2$, and 12 V DC is applied to the anode of the thyristor $SC_2$.

When 12 V DC is applied, since the movable contact $LS_{2s}$ of the relay switch $LS_2$ is closed to the fixed contact $LS_{2a}$, 12 V DC is supplied to the LSI 7 and the coil $LS_{1c}$ of the relay switch $LS_1$ through the relay switch $LS_2$. Then, the timer of the LSI 7 is driven. Further, since the current flows to the coil $LS_{1c}$ of the relay switch $LS_1$ and the movable contact $LS_{1s}$ is closed to the closed contact $LS_{1b}$, the supply of 100 V AC from the AC power supply 8 to the primary $TR_P$ of the high potential transformer TR is stopped.

In the LSI 7, after five seconds the time is driven, the trigger current is supplied to the gate of the thyristor $SC_2$ from the terminal $7_b$. It should be noted that in these five seconds, charges of 12 kV DC charged in the capacitor C are discharged by flowing into the high voltage resistance R and that voltage is dropped to 3 kV. In result, the generation of the arc at the switching of the high voltage reed relays $L_3$, $L_4$ is decreased.

After five seconds elapsed and further after one second, the trigger current is supplied to the gate of the thyristor $SC_3$ from the terminal $7_c$ of the LSI 7. In this one second, the open contacts $L_{3s}$, $L_{4s}$ of the high voltage reed relays $L_3$, $L_4$ are closed before 100 V AC is supplied to the primary $TR_P$ of the high potential transformer TR.

When the trigger current is supplied to the gate of the thyristor $SC_2$ from the terminal $7_b$ of the LSI 7, the thyristor $SC_2$ is turned on, and the current flows to the coils $L_{3c}$, $L_{4c}$ of the high voltage reed relays $L_3$, $L_4$ from the cathode of the thyristor $SC_2$. Then, the open contacts $L_{3s}$, $L_{4s}$ of the high voltage reed relays $L_3$, $L_4$ are closed.

Further, when the trigger current is supplied to the gate of the thyristor $SC_3$ from the terminal 7c of the LSI 7, the thyristor $SC_3$ is turned on, and the current flows to the coil $LS_{2c}$ of the relay switch $LS_2$ from the cathode of the thyristor $SC_3$. Then, the movable contact $LS_{2s}$ of the relay switch $LS_2$ is closed to the fixed contact $LS_{2b}$, and the current supply from the relay switch $LS_2$ to the coil $LS_{1c}$ of the relay switch LS1 is stopped. Accordingly, the movable contact $LS_{1s}$ of the relay switch $LS_1$ is closed to the fixed contact $LS_{1a}$, and 100 V AC is supplied to the primary $TR_P$ of the high potential transformer TR from the AC power supply 8. Then, 9 KV AC is generated at the secondary $TR_s$ of the high potential transformer TR. Further, the generated 9 kV AC is rectified by the diode bridge circuit DB and charged to the capacitor C as 12 kV DC.

In result, the capacitor C of the charges of 12 kV DC is connected to the outlet 4 through the high voltage reed relay $L_3$ at one end and to the ground E through the high voltage reed relay $L_4$ at the other end. Accordingly, the treatment lead 1a outputs 12 kV DC.

The heater 1b for keeping the electric cloth 1 warm heats the electric cloth 1 by the 30 V AC supply from the outlet 4. 30 V AC is supplied from the transformer which is not shown in FIG. 1 as described above. It should be noted that the heater 1b is used while the treatment lead 1a does not output neither 12 kV DC nor 9 kV AC.

Further, it should be noted that 12 kV DC is supplied to the outlet 5 while 12 kV DC is charged in the capacitor C and that 9 kV AC is supplied to the outlet 6 while 9 kV AC is generated at the secondary $TR_s$ of the high potential transformer TR. The electric cloth 2 is plugged to either the outlet 5 or the outlet 6 to output 12 kV DC or 9 kV AC from the treatment lead 2a, respectively.

Furthermore, the heater 3 for keeping warmth is connected to the transformer which is not shown in the figure to heat the electric cloth 2. The supply of 30 V to the heater 3 is supplied from the transformer. It should be noted that the heater 3 is used while the treatment lead 1a does not output neither 12 kV DC nor 9 kV AC.

The DC-AC electric potential treatment apparatus which comprises the above-described circuit configuration and which operates in the above-described way can switch and output the high potential direct current and the high potential alternative current. Therefore, both the electric potential treatment with DC and the electric potential treatment with AC are performed by one DC-AC electric potential treatment apparatus of the present embodiment. Furthermore, there is the arc generation between the contacts in the switch elements but the circuit configuration can prevent the damage of the elements by using the high potential reed relay and the voltage drop function.

The DC-AC electric potential treatment apparatus of the present invention is not limited to the one described in the above embodiment but it can be varied in many ways.

For example, the operation time of the timer of the LSI 7 is five seconds and one second but five seconds can be six or seven or larger, which makes the voltage drop of the capacitor C larger.

Further, the variable circuit, the timer, the power supply circuit for a heater, the element for detecting temperature and switching means disclosed in the Japanese Patent Publication No. 4-28597 may be connected to the circuit of the present embodiment. Accordingly, the treatment lead 1a and the heater 1b can automatically be switched and the output potential of the treatment lead 1a can automatically be switched. Furthermore, AC and DC are switched externally by the double-pole switch S but DC and AC can be formed to be automatically switched.

While the invention has been shown and described with reference to the illustrated embodiment, it should be understood that various changes in form and details may be made without departing from the scope of the invention which is defined in the appended claims.

What is claimed is:

1. A DC-AC electric potential treatment apparatus comprising:
   an electric cloth comprising a treatment lead for outputting AC or DC, wherein said treatment lead is covered with a cloth material;
   an AC power supply;
   a DC-AC power supply circuit for supplying DC or AC to said treatment lead, said DC-AC power supply circuit including a capacitor for charging an electric voltage and a resistor connected to said capacitor in parallel for discharging said electric voltage charged in said capacitor;
   a DC-AC switch circuit for switching the supply from said DC-AC power supply circuit to said treatment lead between DC and AC, said switch circuit including a reed relay connected to an output terminal of DC and AC of said DC-AC power supply circuit and a timer;

a switch for selecting an output of said treatment lead from DC and AC;

a heater for heating said electric cloth and keeping said electric cloth warm; and a power supply circuit for said heater for supplying power supply voltage to said heater, wherein when said switch selects one of DC and AC, the electric current from said AC power supply to said DC-AC power supply circuit is stopped, and said reed relay is closed after a first predetermined time by said timer, then after a second predetermined time the electric current from said AC power supply to said DC-AC power supply circuit is started said selected DC or AC is applied to said treatment lead.

* * * * *